United States Patent [19]
McCandliss

[11] Patent Number: 5,702,474
[45] Date of Patent: Dec. 30, 1997

[54] COAXIAL LIGAMENTED HIP PROSTHESIS

[76] Inventor: Robert McCandliss, 3836 Baywood Dr., Moss Point, Miss. 39563-5006

[21] Appl. No.: 589,644

[22] Filed: Jan. 22, 1996

[51] Int. Cl.$^6$ .................................................. A61F 2/32
[52] U.S. Cl. ................................................. 623/22; 623/23
[58] Field of Search ....................................... 623/22, 23

[56] References Cited

U.S. PATENT DOCUMENTS 2,765,787   10/1956   Pellet .......................................... 623/23

Primary Examiner—Randy C. Shay
Attorney, Agent, or Firm—Roger A. Marrs

[57] ABSTRACT

A hip prosthesis is disclosed herein intended to be fitted into a skeletal pelvis socket and which has a replacement socket that includes a metal semi-spherical acetabulum base with a plastic acetabulum liner for movably holding a spherical ball against the liner by a ligament rod. The rod passes through a head of a stem implanted into a femur and terminates with a ligament anchor plate fitted in the acetabulum base via an eyelet and pin connection. A tensioning nut is carried on the stem head in threadable connection with the rod. A conical cutout in the spherical ball permits movement of the ball with the apex of the cone at the center of the spherical ball under adjustable tensioning of the rod. A wear compensation system is included by incorporating an open passageway in the base which communicates with a blister in the liner for accommodating the introduction of cement to compensate for wear. A boot of mesh material encloses portions of the base, liner and the ball.

11 Claims, 1 Drawing Sheet

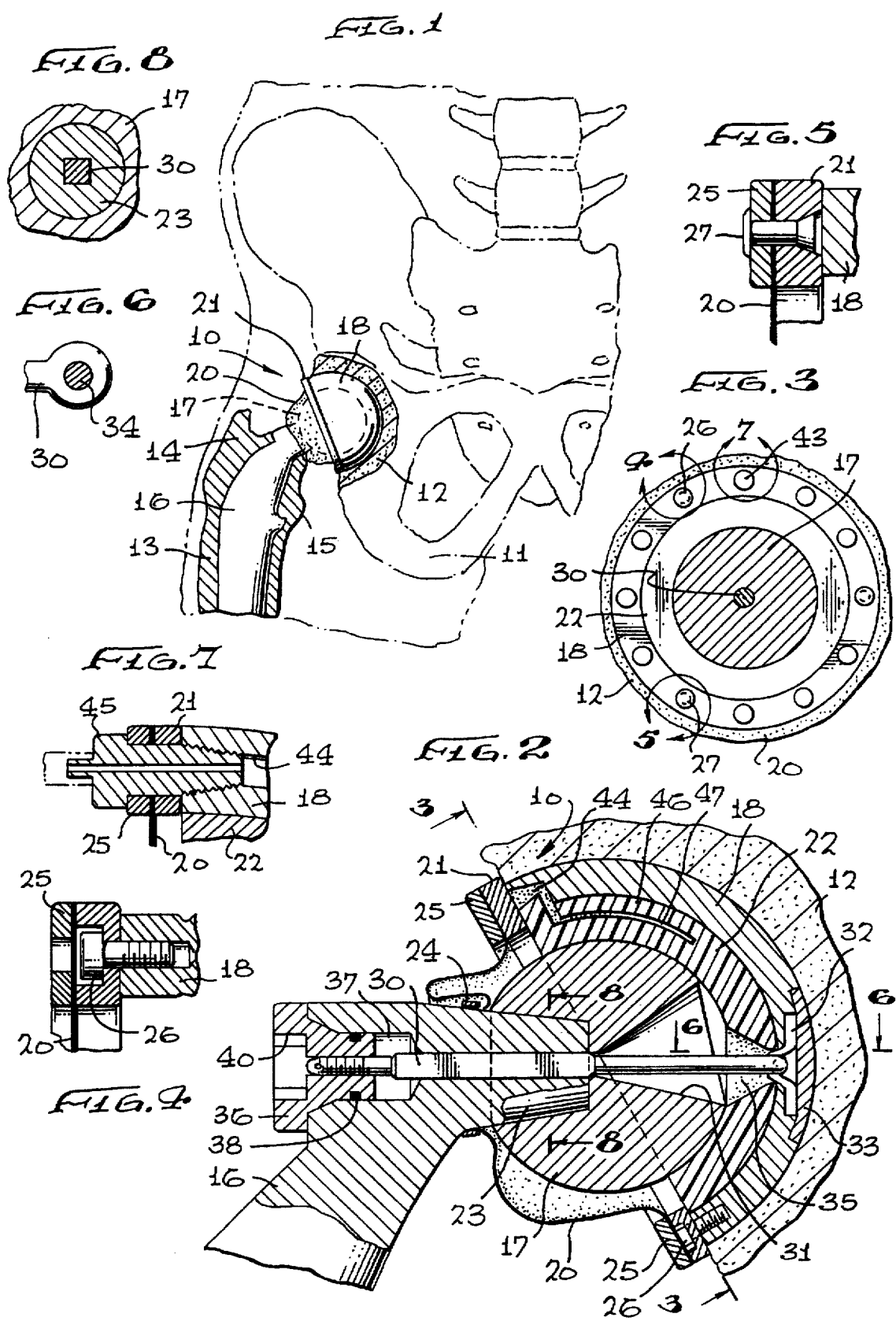

COAXIAL LIGAMENTED HIP PROSTHESIS

BACKGROUND OF THE INVENTION

1. Field of the Invention

The present invention relates to the field of hip prosthesis, and more particularly to a novel replacement connection between a skeletal femur and pelvis socket that permits a substantial degree of articulation and includes wear particle containment as well as a wear compensation system.

2. Brief Description of the Prior Art

In the past, hip replacement devices and systems have been employed so that a person may have normal mobility with respect to leg movement. Problems and difficulties have been encountered when employing conventional hip replacement devices which stem largely from the fact that such devices provide limited rotational movement and stability. For example, conventional hip prosthesis will not permit a person to sit cross-legged with comfort or even at all without dislocation of the prosthesis and redoing the surgery. Furthermore, no provisions are made for subsequent surgery which may be required due to excessive wear on the component parts. Usually, subsequent surgery requires complete replacement of the prosthesis. Also, conventional hip prosthesis will not permit for deflection of debris or particles of components which are ground loose from adjacent components when the joint is articulated.

Therefore, a long-standing need has existed to provide a novel hip prosthesis which will readily provide for torsional loading and which provides rotational stability over a wide angular range. Additional means should be incorporated into such a prosthesis which not only provides for particle collection which is due to wear and which will also compensate for wear conditions between moving parts.

SUMMARY OF THE INVENTION

Accordingly, the above problems and difficulties are avoided by the present invention which provides a novel hip prosthesis having a ball joint adapted to be placed into a pelvis socket, which includes a semicircular base having a lining defining a socket into which a ball is movably carried. The ball is secured to the end of a stem head at one end while a ligament tensioning means is carried on the head of the stem and passes through the ball, terminating in an anchor connection with the base. The opposite end of the ligament rod includes a square cross-section length and a threaded section engaging a threaded nut rotatable against the head of the stem to provide adjust accordingly. An elongated portion of the stem is implanted into the shaft of a femur. The ball includes a conical recess with its apex at the center of the sphere through which the ligament rod passes so that the ball may rotate through a wide angle of articulation within the liner of the base without stretching the ligament rod. A close-mesh boot is disposed about the exposed portion of the ball in order to collect debris and particles which may be ground from component parts during articulation of the joint. A retaining means is employed for holding the boot in place and for securement of the component parts together.

Means are further provided on the base for accommodating cement that may be forced into a compensation blister within the base and liner without necessity of boot removal.

Therefore, it is among the primary objects of the present invention to provide an adjustable ligament rod within a hip joint prosthesis that provides positive restraint against dislocation when in use by a recipient.

Another object of the present invention is to provide a hip prosthesis which may move at extreme angles of rotation about a femur axis, or in a lateral direction, a ligament tends to be stretched providing increased elastic resistance to further travel.

Still, a further object of the present invention is to provide a hip prosthesis wherein the ligament length remains unchanged during normal rotations of the ball joint in the acetabulum in the lateral plane, about the femur axis, or in the front-to-back plane, due to the ligament guide point location at the center of the spherical ball.

Another object resides in including a ligament accommodation for rotation about the horizontal, lateral (Y-Y) by torsion between the ligament-guide-point and the ligament anchoring pin.

Yet another object of the present invention is to provide a novel hip prosthesis which permits subsequent adjustment or renewal of component part fit by providing axis passageway through which cement can be introduced under local anesthesia.

Another object of the present invention is to provide a novel coaxial ligamented hip prosthesis having wear-particle containment boot and which further includes wear compensation system whereby subsequent adjustment or compensation can be made due to wear of component parts.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

FIG. 1 is a diagrammatic view of a skeletal pelvis and femur connected together by the novel hip prosthesis of the present invention;

FIG. 2 is an enlarged cross-sectional view of the replacement connection between the femur and socket of the pelvis shown in FIG. 1;

FIG. 3 is a transverse cross-sectional view of the connection shown in FIG. 2 as taken in the direction of arrows 3—3 thereof;

FIG. 4 is an enlarged fragmentary cross-sectional view of a connection screw holding the retainer to the base, as shown by the circles indicated by numeral 4 in FIG. 3;

FIG. 5 is an enlarged fragmentary cross-sectional view of a rivet connection between the retainer ring and the peripheral edge of the boot, as shown by numeral 5 in FIG. 3;

FIG. 6 is an enlarged fragmentary cross-sectional view as taken in the direction of arrows 6—6 Of FIG. 2 illustrating the ligament rod attachment;

FIG. 7 is a fragmentary cross-sectional view of the wear compensation means utilized in the present invention for introducing cement into a passageway encircled by the numeral 7 in FIG. 3; and FIG. 8 is a fragmentary cross-sectional view of the square cross-section of the ligament rod contained within the square hole in the shank of the prosthesis.

DESCRIPTION OF THE PREFERRED EMBODIMENT

Referring to FIG. 1, the novel hip prosthesis of the present invention is illustrated in the general direction of arrow 10 and the prosthesis is illustrated as being mounted in a socket area of a pelvis bone 11 and the area is indicated by numeral 12. The hip prosthesis connects the socket area 12 with a femur 13. The great trochanter is indicated by numeral 14 while the lesser trochanter is indicated by numeral 15. The head of the femur 13 has been removed so as to accommodate the hip prosthesis. The prosthesis includes a fixed member taking the form of a shaft 16 which is implanted into the femur 13 which supports a ball 17 projecting into a semicircular acetabulum base 18 which is secured by conventional means to the pelvic socket area 12. Part of the ball 17 is exposed from the base 18 and is fixedly secured to the shank of the prosthesis 16. The exposed portion of the ball 17 is covered by a closed mesh boot 20 so that particles or debris may be collected in the boot due to wear between component parts. The boot 20 is maintained on the base 18 about its peripheral edge by means of a retainer 21.

Referring now in detail to FIG. 2, it can be seen that the acetabulum base 18 is composed of metal and includes an inner curved surface which is lined by a plastic acetabulum liner 22. The outer surface of the ball 17 is movably disposed with respect to the surface of the liner 22 and the ball 17 is secured to the terminating end of shaft 16 by means of a wedged fit with a projection 23 inserted into a hole and terminating at the middle of the ball. Securement may be achieved through the use of adhesives or the like. It is to be seen that the boot 20 is fastened about the projection 23 by means of a clamp 24 and to the retainer 21 by an outer retainer ring 25. The edge peripheral region of the boot 20 is disposed between the inner retaining ring 21 and the outer retaining ring 25 and a plurality of fasteners are employed to secure the boot to the base 18, such as by screw 26. Such a screw is illustrated in FIG. 4. In this FIGURE, it can be seen that the retainer 21 is held in position and releasable securement with the base 18.

Referring to FIG. 3, the outer retaining ring 25 is held in position by means of a rivet 27 which couples the outer retaining ring 25 to the inner retaining ring 26 and the peripheral edge marginal region of the boot 20 is held between the opposing surfaces of the retaining rings.

Referring now in detail to FIG. 2, it can be seen that the base 18 is implanted into the socket area 12 of the pelvis bone. The upper end of shaft 16 terminates in a frustroconical portion 23 that is press-fitted into a mating cavity in the ball 17. If desired, adhesive may also be employed. Furthermore, a ligament rod 30 extends through the head 23 of the stem 16 having one end thereof passing through a conical cutout or recess within the spherical ball 17. The conical cutout or recess is identified by numeral 31. The end of ligament rod 30 terminates in a connection 32 which is carried on an anchor plate 33 by means of an eyelet which passes through a hole in the end of the rod 30. Such a connection is illustrated in FIG. 6 wherein the eyelet is represented by numeral 34. A conical opening 35 in the liner 22 further accommodates passage of the rod from the head 23 through the conical recess 31 and the recess 35. The opposite end of rod 30 terminates in threaded connection with a ligament tensioning nut 36 that is seated in a receptacle 37 in the head 23. As the nut 36 is rotated, tension is applied to the rod 30 to tighten or loosen its connection with the base 18 via the anchor plate 33. An "O" ring provides a friction lock and seal and the ring is indicated by numeral 38. The exposed end of the nut 36 may be configured with a hex opening 40 in order to receive a suitable wrench for accomplishing rotation of the nut within the chamber 37.

FIG. 2 also illustrates the retention of one marginal edge of the boot 20 to the head 23 by means of a clamp or the like 24. The opposite edge marginal region of the boot is captured between the opposing surfaces of the inner and outer rings 21 and 25 respectively. Preferably, the acetabulum 18 is composed of a metal material while the acetabulum liner 22 is composed of a plastic material, such as a polyethylene material. The close meshed boot 20 is composed of a dacron mesh.

A wear compensation system is employed as part of the present invention which permits the liner 22 or at least a portion thereof to expand in order to take up any slack or looseness caused by wearing between the surfaces of the ball 17 and the opposing surface of the liner 22. As wear occurs, particles may be dislodged from either of the two components and these particles are captured by the boot 20. In order to expand a portion of the boot into closer contact with the surface of the ball, the compensation system includes an opening 42, as shown in FIG. 3, which leads to an internal passageway 44 in the base 18 so that a fitting 45, as shown in FIG. 7, can be placed into the opening 43 in order to introduce a cement material into the passageway 44. The fitting 45 passes through an opening in both the inner and outer retaining rings 21 and 25 so that the tapered and threaded nozzle of the fitting 45 can fit properly into the passageway 44. As shown in FIG. 2, the passageway 44 is in communication with a slit chamber or blister 46 in the liner 22. As the material is introduced to the chamber or blister 46, expansion occurs between the separated components of the liner 22 causing the liner component, identified by numeral 47, to expand against the surface of the ball 17.

In FIG. 3, it can be seen that the hole 43 is open through the base 18 and that the screw 26 passes through both the retainer rings. The rivet 27 illustrated in FIG. 5 holds the retaining rings in clamping relationship with the edge marginal region of the outer peripheral region of boot 20.

In view of the foregoing, it can be seen that the ligament rod 30 provides positive restraint against hip prosthesis dislocation regardless of orientation whether the person is walking or whether the person may be in a sitting position with legs crossed. The ligament rod 30 tends to be stretched or tensioned so as to provide increased elastic resistance to further travel which would cause dislocation at extreme angles or rotation about the femur axis or in the lateral direction.

Furthermore, the ligament length of the rod remains unchanged during normal rotation of the ball 17 in the acetabulum in the lateral plane about the femur axis or in the front-to-back plane because of the ligament guide point location at the center of the spherical ball. The ligament rod accompanies rotation about the horizontal, lateral (Y-Y) axis by torsion between the ligament guide point and the ligament anchoring pin. The ligament anchor pin retainer plate prevents polyurethane wear fragments from getting into tissue behind the acetabulum and causing inflammation.

Any tension or slack ligament adjustment is achieved by rotation of the ligament tensioning nut and Allen type wrench inserted into the hexagon hole at the exposed end of the nut.

With respect to the wear compensation system, the slit chamber Dr blister in the polyethylene liner and the associated flow passageway through the metallic base provide for the introduction of cement, under pressure, into the chamber or blister, forcing the worn innersurface of the liner radially inward so as to eliminate the excessive clearance caused by the wear and, therefore, to re-establish the spherical configuration at the top of the polyethylene liner.

The Dacron flexible boot Which may be a sheet which is woven, knitted or crocheted, is disposed between the prosthesis tapered shank supporting the sphere noted as being the head of the shaft 16 and the metallic rim of the base wherein the structure serves to confine the polyethylene wear particles, or foreign matter which reside inside the joint and the boot prevents migration to the surrounding tissue and the subsequent inflammation.

The subsequent surge involved in compensation for wear is expected to be required in 10 to 20 years after prosthesis implant and this may be achieved under local anesthesia. Only an incision is required to provide access to the threaded socket in the upper metallic acetabulum base for the introduction of cement under pressure via the tapered nut. The rest of the prosthesis is not disturbed and minimal rehabilitation after surgery may be required.

The inventive prosthesis requires precise angular positioning of the acetabulum assembly in the pelvis machine socket so as to permit conical opening in the spherical ball to clear the ligament rod at all normal angles of rotation about all three axes. The square cross-section portion Of the ligament rod prevents torsion of the ligament rod during Walking from loosening the nut retaining the ligament rod. Also, it provides torsional restraint to the ligament rod while a surgeon is tightening the nut.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A hip socket prosthesis for disposal between a skeletal femur and a pelvis socket comprising:

a metal semi-spherical acetabulum base;

a spherical ball;

a plastic acetabulum liner disposed in said metal semi-spherical acetabulum for movably holding said spherical ball;

an elongated stem having a head laterally projecting into securement with said spherical ball; and a ligament rod movably carried on said head and secured to said metal semi-spherical acetabulum base for movably holding said spherical ball.

2. The invention as defined in claim 1 wherein:

said spherical ball includes a recess occupied by said head and a conical opening coaxially disposed with respect to said head having its apex terminating at said head and outwardly flaring to terminate opposite said lining; and said ligament rod having opposite ends separated by a midsection movable through said head;

one end of said ligament rod passing through said conical recess to be anchored with said metal semi-spherical acetabulum base.

3. The invention as defined in claim 2 wherein:

said end of said ligament rod opposite to said one end is externally exposed within said head, and means operably coupled to said end and bearing against said head for selectively and manually moving said head about said ligament rod to urge said spherical ball into engagement with said liner.

4. The invention as defined in claim 3 wherein:

said moving means is a tensioning nut for adjusting the engagement force of said spherical ball against said liner.

5. The invention as defined in claim 4 including:

a boot of mesh material carried between said head and said metal semi-spherical acetabulum base about said spherical ball for collecting debris worn from said liner, said base and said Spherical ball during use.

6. The invention .as defined in claim 5 including:

a wear compensation means having an expandable portion provided in said liner; and said base having an open passageway leading to said expandable portion for introducing an injected cement into said expandable portion urging said liner into forcible engagement with said spherical ball.

7. The invention as defined in claim 6 wherein:

said liner includes a central opening accommodating said ligament rod and said anchoring connection with said metal semi-spherical acetabulum base.

8. A replacement hip prosthesis for fitting into a skeletal pelvis socket comprising:

an elongated stem with a laterally projecting held;

an arcuate socket base with an internal liner;

a ball secured to said head and bearing against said liner; and a ligament rod carried on said head and slidably extending through said ball terminating in an anchored connection with said socket base.

9. The invention as defined in claim 8 including:

tension adjustment means disposed between said ligament rod and said head for selectively adjusting the bearing force applied by said ball to said liner.

10. The invention as defined in claim 8 including:

a flexible mesh boot having opposite ends secured to said head and to said socket base respectively for collecting debris dislodged from said liner, said ball and said socket base during use.

11. The invention as defined in claim 8 including:

means cooperating between said socket base and said liner for expanding said liner into close load bearing relationship with said ball.

* * * * *